United States Patent [19]  [11] 4,097,668
Benkó et al.  [45] Jun. 27, 1978

[54] 2-[(P-METHOXY-BENZOYL)-HYDRAZONO-FORMYL]-QUINOXALINE-1,4-DIOXIDE

[75] Inventors: Pál Benkó; Ildiko Simonek; László Pallos; Jenö Kovács; Károly Magyar, all of Budapest, Hungary

[73] Assignee: Egyt Gyogyszervegyeszeti Gyar, Budapest, Hungary

[21] Appl. No.: 775,998

[22] Filed: Mar. 9, 1977

Related U.S. Application Data

[63] Continuation-in-part of Ser. No. 630,762, Nov. 11, 1975, abandoned.

[30] Foreign Application Priority Data

Nov. 21, 1974  Hungary ............................. EE 2278

[51] Int. Cl.$^2$ ................ C07D 241/00; A61K 31/085; A61K 31/165; A61K 31/495
[52] U.S. Cl. .................................... 542/418; 424/250
[58] Field of Search ................ 542/418; 260/250 QN, 260/562 H

[56] References Cited

U.S. PATENT DOCUMENTS

| | | | |
|---|---|---|---|
| 2,767,174 | 10/1956 | Katz et al. | 260/240 G |
| 3,371,090 | 2/1968 | Johnson | 260/250 QN X |
| 3,493,572 | 2/1970 | Johnson | 260/250 QN |
| 3,793,323 | 2/1974 | Seng et al. | 260/250 QN X |
| 3,819,616 | 6/1974 | Seng et al. | 260/240 G |
| 3,840,600 | 10/1974 | Eberle | 260/562 H |
| 3,881,009 | 4/1975 | Seng et al. | 260/250 QN UX |

FOREIGN PATENT DOCUMENTS 1,058,047  2/1967  United Kingdom.

*Primary Examiner*—Daniel E. Wyman
*Assistant Examiner*—Thomas A. Waltz
*Attorney, Agent, or Firm*—Young & Thompson

[57] ABSTRACT

The invention provides 2-[(p-methoxy-benzoyl)-hydrazono-formyl]-quinoxaline-1,4-dioxide.

This compound is indicated for use as a potent antibacterial agent having a low toxicity.

1 Claim, No Drawings

2-[(P-METHOXY-BENZOYL)-HYDRAZONO-FORMYL]-QUINOXALINE-1,4-DIOXIDE

This is a continuation-in-part application of application Ser. No. 630,762 filed on Nov. 11, 1975, now abandoned.

The present invention relates to a novel heterocyclic compound. More particularly the invention provides 2-[(p-methoxy-benzoyl)-hydrazone-formyl]-quinoxaline-1,4-dioxide of the formula

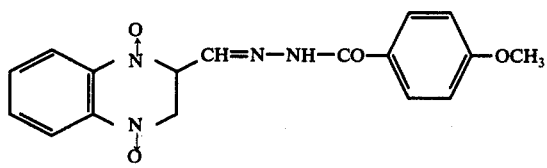

and its pharmaceutically acceptable acid addition salts.

The compound according to the invention has excellent bactericidal (antibacterial) properties wherein its toxicity is very low. The bactericidal effect was investigated with the following bacterium strains:

1. *Pseudomonas pyocyanaea* 14K
2. *Proteus vulgaris* A.H.
3. *Bacillus subtilis* ATCC 6633
4. *Salmonella Typhi murium*
5. *Shigella Sonnei*
6. *Staphylococcus areus* Duncan
7. *Staphylococcus areus* 209 P.
8. *Escherichia coli* 0111

The lowest concentration inhibiting the multiplication of the test bacteria (MIC, mg./ml.) was determined in vitro. The antibacterial effect of the claimed compound was compared with that of known quinoxaline-1,4-dioxide derivatives, further of known and in the therapy extensively used compounds, such as Thiamphenicol [dichloro-N-(2-hydroxy-1-hydroxymethyl-2-/p-methane-sulphonyl-phenyl/-ethyl)-acetamide] and nitrofurantoin (3-/5-nitrofurfurylidene-amino/-hydantoin).

The in vitro MIC values determined in this way as well as the peroral $LD_{50}$ values determined on mice are given in the following Table I.

This excellent bactericidal effect is surprising especially when compared with the similar effect of 2-(benzoyl-hydrazono-formyl)-quinoxaline-1,4-dioxide because, as shown in Table I, the introduction of a p-methoxy group into the molecule results in an increase of the effect of two orders of magnitude e.g. against the strain Escherichia coli 0111.

The compound according to the invention may be converted into its acid addition salts by reaction with pharmaceutically acceptable organic or inorganic acids in a manner known per se. Examples of acids which may be used for acid addition salts formation are: hydrochloric, hydrobromic, sulfuric, phosphoric, fumaric, maleic, malic, acetic and tartaric acid.

The claimed compounds may be used as pharmaceuticals on their own or in the form of appropriate medicinal preparations for administration e.g. enterally or parenterally. In order to produce suitable medicinal preparations the compound is worked up with organic or inorganic adjuvants which are inert and physiologically acceptable. Examples of such adjuvants are lactose, starch, talc and stearic acid for tablets and dragees; solutions of sugar and glucose for syrups; water, alcohols, glycerin and vegetable oils for injectable solutions; and natural or hardened oils and waxes for suppositories.

The pharmaceutical preparations may furthermore contain suitable preserving, stabilizing and wetting agents, solubilizers, sweatening and coloring substances or flavorings.

The term "in a manner know per se" as used herein designates methods in use or described in the literature on the subject.

The compound of the invention can be prepared, for example, as follows:

11.8 g (0.05 moles) of 2-formyl-quinoxaline-1,4-dioxide-dimethylacetal are suspended in 75 ml. of water. 4 ml. of concentrated aqueous hydrochloric acid are added. The obtained mixture is boiled for 10 minutes and then the suspension of 8.3 g. (0.05 moles) of p-methoxy-benzoic acid hydrazide in 50 ml. of warm water is added. The reaction mixture is allowed to cool to room temperature and stirred for 3 hours at this temperature. The separated product is filtered and then washed with water and ethanol. The 2-[(p-methoxy-benzoyl)-hydrazono-formyl]-quinoxaline-1,4-dioxide is Table I

| Compound | $LD_{50}$ mg./kg. | MIC values in mg./ml. with bacterium strains | | | | | | | |
|---|---|---|---|---|---|---|---|---|---|
| | | 1 | 2 | 3 | 4 | 5 | 6 | 7 | 8 |
| 2-[(p-Methoxy-benzoyl)-hydrazono-formyl-]-quinoxaline-1,4-dioxide | 10,000 | 1.9 | 1.9 | 1.9 | 1.9 | 3.9 | 3.9 | 3.9 | 0.9 |
| 2-(Methoxy-carbonyl-hydrazono-formyl)-quinoxaline-1,4-dioxide (Carbadox) (comparative compound on the basis of US Pat. No. 3,493,572) | 4,000 | 100 | 25 | 5 | 50 | 10 | 75 | 100 | 25 |
| 2-(Hexyl-carbonyl-hydrazono-formyl)-quinoxaline-1,4-dioxide (comparative compound on the basis of British Pat. No. 1,058,047) | 4,000 | 100 | 100 | 100 | 100 | 100 | 75 | 100 | 100 |
| 2-(Benzoyl-hydrazono-formyl)-quinoxaline-1,4-dioxide (comparative compound on the basis of British Pat. No. 1,058,047) | 4,000 | 100 | 100 | 100 | 100 | 100 | 100 | 100 | 100 |
| Thiamfenicol (comparative compound) | 15,000 | 15.6 | 15.6 | 31.2 | 31.2 | 62.5 | 62.5 | 62.5 | 62.5 |
| Nitrofurantoin (comparative compound) | 895 | 7.8 | 15.6 | 31.2 | 7.8 | 31.2 | 62.5 | 31.2 | 31.2 |

It appears from Table I that the compound according to the invention is, depending on the tested bacterium strain, 8 to 70 times more effective than Thiamphenicol and generally 25 to 50 times more potent than the tested known quinoxaline-1,4-dioxide derivatives but its toxicity is 2.5 times lower.

obtained with a yield of 79%; m.p.: 260° C.

What we claim is:

1. 2-[(p-Methoxy-benzoyl)-hydrazono-formyl]-quinoxaline-1,4-dioxide and its pharmaceutically acceptable acid addition salts.

* * * * *